US010086027B1

(12) United States Patent
Elgamal et al.

(10) Patent No.: US 10,086,027 B1
(45) Date of Patent: Oct. 2, 2018

(54) GREEN SYNTHESIS OF KATONONIC ACID NANOSHEETS

(71) Applicant: KING SAUD UNIVERSITY, Riyadh (SA)

(72) Inventors: Ali Ali Hassan Elgamal, Talkha (EG); Manal Ahmed Gasmelseed Awad, Riyadh (SA); Rabab El Dib, Giza (EG); Shaza Mohamed Adel Al-Massarani, Riyadh (SA); Omer Ahmed Basudan, Al Azizyah (SA)

(73) Assignee: KING SAUD UNIVERSITY, Riyadh (SA)

( * ) Notice: Subject to any disclaimer, the term of this patent is extended or adjusted under 35 U.S.C. 154(b) by 0 days.

(21) Appl. No.: 15/909,939

(22) Filed: Mar. 1, 2018

(51) Int. Cl.

| | |
|---|---|
| ***A61K 36/185*** | (2006.01) |
| ***A61K 9/70*** | (2006.01) |
| ***A61P 35/00*** | (2006.01) |
| ***A61P 31/10*** | (2006.01) |
| ***A61P 31/04*** | (2006.01) |

(52) U.S. Cl.
CPC .......... *A61K 36/185* (2013.01); *A61K 9/7007* (2013.01); *A61P 31/04* (2018.01); *A61P 31/10* (2018.01); *A61P 35/00* (2018.01); *A61K 2236/39* (2013.01); *A61K 2236/51* (2013.01)

(58) Field of Classification Search
None
See application file for complete search history.

(56) References Cited

U.S. PATENT DOCUMENTS

| | | | | |
|---|---|---|---|---|
| 9,974,750 | B1 * | 5/2018 | Al-Massarani ........ | A61K 31/56 |
| 2009/0028969 | A1 | 1/2009 | Sene | |

OTHER PUBLICATIONS

Al-Massarani et al., "New Cytotoxic Seco-Type Triterpene and Labdane-Type Diterpenes from Nuxia oppositifolia," Molecules 22(3), 389 (2017).

* cited by examiner

*Primary Examiner* — Michael Barker
(74) *Attorney, Agent, or Firm* — Richard C. Litman

(57) ABSTRACT

The synthesis of katononic acid nanosheets is a method of extraction of katononic acid from the n-hexane fraction of *Nuxia oppositifolia*. The katononic acid isolated from *N. oppositifolia* may be suspended in methanol and added dropwise to boiling water, sonicated, stirred, and freeze dried to form katononic acid nanosheets. These katononic acid nanosheets may be used to kill cancer cells or microorganisms.

13 Claims, 5 Drawing Sheets

Acc. Voltage: 100 kV | Mag.: 50000 x | 50 nm
FIG. 2
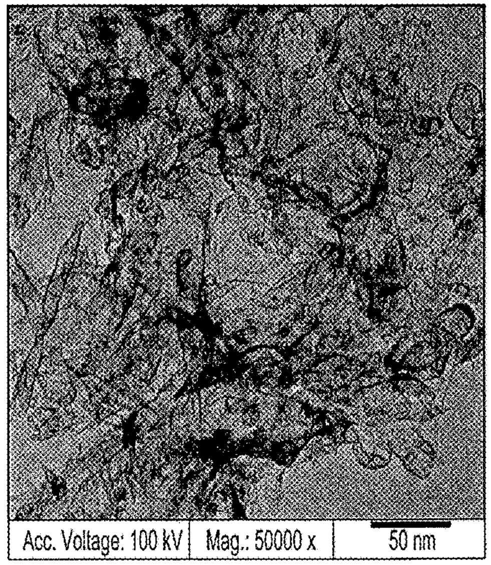
FIG. 3
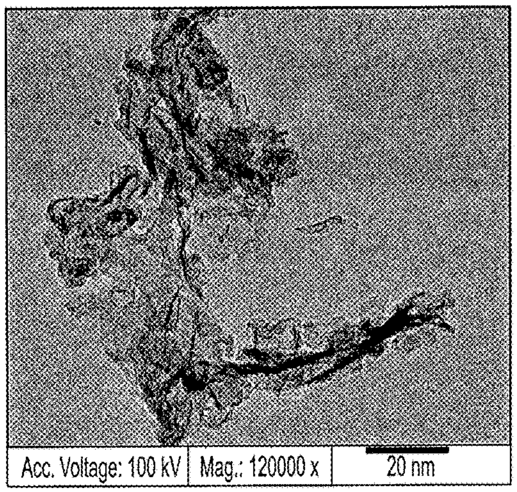
FIG. 4
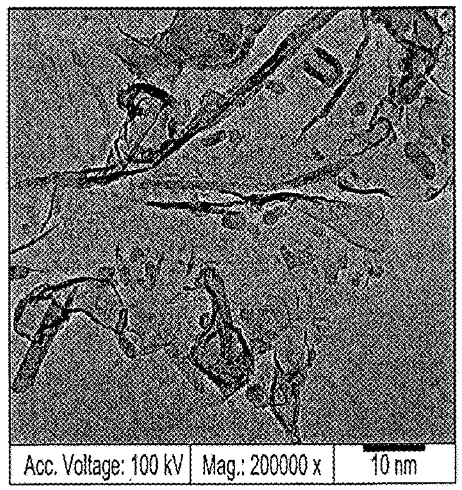
FIG. 5

GREEN SYNTHESIS OF KATONONIC ACID NANOSHEETS

BACKGROUND

1. Field

The disclosure of the present patent application relates to katononic acid nanosheets, and particularly to a method of green synthesis of katononic acid nanosheets.

2. Description of the Related Art

According to some estimates, cancer is responsible for around 15% of annual deaths world-wide. Traditionally, cancer treatment focused on chemotherapy, radiation therapy, surgery, and palliative care. Many cancers cannot be removed surgically, and chemotherapy and radiation often produce such severe side effects that they must be discontinued prior to achieving clearance.

Recently, a variety of new cancer therapies have been developed, including immunotherapies and new pharmaceuticals with fewer side effects. Immunotherapies show promise for some patients, but do not work for everyone and at times can result in extreme side effects. New pharmaceuticals are a promising area of research, including pharmaceuticals derived from green sources.

In materials science, nanomaterials have demonstrated unique, size and morphology based characteristics. Nanobiotechnology is an emerging field demonstrating significant potential for the development of new medicines.

Thus, a method of green synthesis of katononic acid nanosheets solving the aforementioned problems is desired.

SUMMARY

The green synthesis of 3-Oxoolean-12-en-29-oic acid (katononic acid) nanosheets includes extraction of katononic acid from the n-hexane fraction of *Nuxia oppositifolia*. The katononic acid isolated from *N. oppositifolia* may be suspended in methanol and added dropwise to boiling water, sonicated, stirred, and freeze dried to form katononic acid nanosheets.

In an embodiment the katononic acid nanosheets may be used to kill cancer cells. The cancer cells may be breast cancer, liver cancer, colon cancer, lung cancer, or cervical cancer cells. The cancer cells may be human cancer cells.

In an embodiment the katononic acid nanosheets may be used to kill microbes. The microbes may be gram positive bacteria, gram negative bacteria, or fungi.

These and other features of the present disclosure will become readily apparent upon further review of the following specification and drawings.

BRIEF DESCRIPTION OF THE DRAWINGS

FIG. 2 is a transmission electron micrograph of katononic acid nanosheets.

FIG. 3 is a further transmission electron micrograph of katononic acid nanosheets.

FIG. 4 is a further transmission electron micrograph of katononic acid nanosheets.

FIG. 5 is a further transmission electron micrograph of katononic acid nanosheets.

Similar reference characters denote corresponding features consistently throughout the attached drawings.

DETAILED DESCRIPTION OF THE PREFERRED EMBODIMENTS

Figure 1:
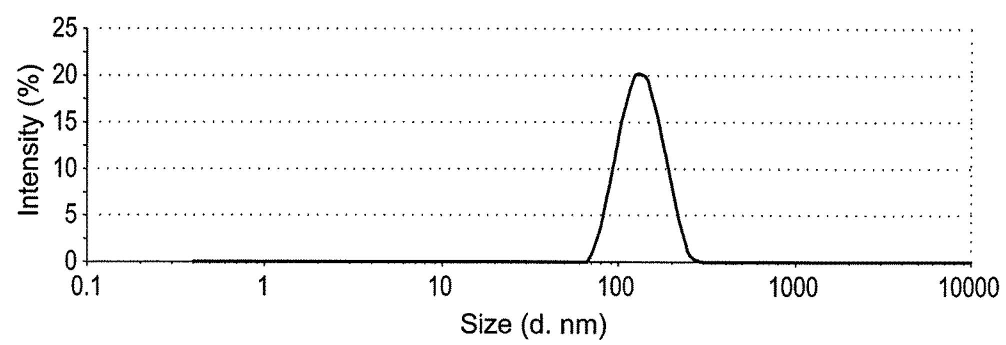
FIG. 1 is a graph of the size distribution curve of katononic acid nanosheets.

Green synthesis of katononic acid nanosheets includes extraction of katononic acid from *Nuxia oppositifolia*, e.g., from an n-hexane fraction of *Nuxia oppositifolia*. The katononic acid isolated from *N. oppositifolia* may be suspended in an alcohol, e.g., methanol and added dropwise to boiling water, sonicated, stirred, and freeze dried to form katononic acid nanosheets.

In an embodiment, the katononic acid may be extracted from *N. oppositifolia* harvested in Wadi Lajab, in the Jazan province of Saudi Arabia. The extraction may be performed using the aerial parts of *N. oppositifolia*, such as the leaves, stems, and/or flowers. The aerial parts of *N. oppositifolia* may be dried, powdered, and extracted by maceration. The maceration may be performed in an alcohol, e.g., ethanol, to produce an ethanolic extract. The ethanolic extract may be filtered, concentrated, and dried. The dried ethanolic extract may then be resuspended in ethanol and partitioned, e.g., partitioned with n-hexane, chloroform, and n-butanol, to form one or more *N. oppositifolia* fractions. At least one *N. oppositifolia* fraction may be further separated using column chromatography. For example, the n-hexane fraction may be further separated using column chromatography and eluted with an n-hexane-ethyl acetate gradient. The subfraction eluted with 10% EtOAc/n-hexane may be crystallized to produce powdered katononic acid.

In an embodiment, katononic acid nanosheets may be synthesized by dissolving powdered katononic acid in methanol to provide a mixture, adding the mixture dropwise to boiling water, sonicating the resulting mixture, and then stirring and freeze drying the mixture.

In an embodiment, the katononic acid nanosheets may be used to kill cancer cells. The cancer cells may be breast cancer, liver cancer, colon cancer, lung cancer, or cervical cancer cells. The cancer cells may be human cancer cells. The cancer cells may be killed by exposure to katononic acid nanosheets at a concentration ranging from about 3.125 μg/ml to about 100 μg/ml. The cancer cells may be killed by administration of an effective dose of katononic acid nanosheets at a concentration ranging from about 3 μg/ml to about 100 μl/ml, e.g., about 3.125 μg/ml, about 6.25 μg/ml, about 12.5 μg/ml, about 12.5 μg/ml, about 25 μg/ml, about 50 μg/ml, or about 100 μl/ml.

In an embodiment, the katononic acid nanosheets may be used to kill microbes. The microbes may include gram positive bacteria, gram negative bacteria, and/or fungi. The fungi may include at least one of *Absidia corymbifera, Geotricum candidum*, and *Candida albicans*. The gram positive bacteria may include at least one of *Staphylococcus aureus, Staphylococcus epidermidis*, and *Streptococcus pyogenes*. The gram negative bacteria may include at least one of *Proteous vulgaris, Klebsiella pneumoniae*, and *Salmo-*

*nella enteritidis*. The microbes may by killed by administration of an effective dose of katononic acid nanosheets.

The following examples illustrate the present teachings.

Example 1

Compound Isolation and Identification

Katononic acid was obtained from the n-hexane fraction of the aerial parts of the Saudi plant *N. oppositifolia*, following the application of a number of chromatographic purification techniques. Briefly, aerial parts of *N. oppositifolia* (leaves, stems, and flowers) were collected from Wadi Lajab in Jazan province of Saudi Arabia and dried and powdered. The dried and powdered aerial parts were then extracted by maceration in 80% ethanol at room temperature. The combined ethanolic extract was then filtered and concentrated under reduced pressure at 40° C. using a rotary evaporator, producing 105 g dried ethanolic extract. The dried ethanolic extract (105 g) was then dissolved in 40% ethanol and successively partitioned with n-hexane (3×500 mL), chloroform (3×500 mL), and n-butanol (3×500 mL) to produce extracts. The n-hexane fraction (17.6 g) was separated using column chromatography on pre-packed silica gel columns (40 mm i.d.×350 mm) and eluted with an n-hexane-ethyl acetate gradient. Fractions were examined using thin layer chromatography and those with similar characteristics were pooled, producing four fractions (A-D). Subfraction A was eluted with 5% EtOAc/n-hexane, subfraction B was eluted with 10% EtOAC/n-hexane, subfraction C was eluted with 20% EtOAc/n-hexane, and subfraction D was eluted with 30% EtOAc/n-hexane. Subfraction B was crystallized to isolate powdered katononic acid.

Example 2

Synthesis of Katononic Acid Nanosheets

Powdered katononic acid (50 mg) produced by the method of Example 1 was dissolved in about 10 ml methanol to produce Solution A. Water (40 ml) was boiled, and about 5 ml of Solution A was added dropwise to the boiled water, with a flow rate of about 0.1-0.3 ml per minute for about 10 minutes, under ultrasonic conditions. After sonication for about 20 minutes the mixture was stirred for about 15 minutes and freeze-dried to produce katononic acid nanosheets. The nanosheets were characterized using a Zetasizer Nano series HT Laser, ZEN3600 (Molvern Instrument, UK), to determine the average size of the resulting nanosheets (FIG. 1). Transmission electron microscopy (TEM, JEM-1400, JEOL, Japan) was employed to characterize the size, shape and morphologies of nanosheets (FIGS. 2-5).

Example 3

Cytotoxicity Testing

The cytotoxic effect of the synthesized nanosheets was evaluated against five cancer cell lines, including breast carcinoma cells (MCF-7), hepatocellular carcinoma cells (HepG-2), human colon carcinoma cells (HCT-116), human lung adenocarcinoma epithelial cells (A549), and cervical carcinoma cells (Hela). For each tested concentration of nanosheets, at least three replicates were tested. The mean viability of the cancer cells was calculated and used to determine the percent inhibition and $IC_{50}$. The results of these tests are provided in Tables 1-5 and illustrated in FIGS. 6-10.

Figure 6:
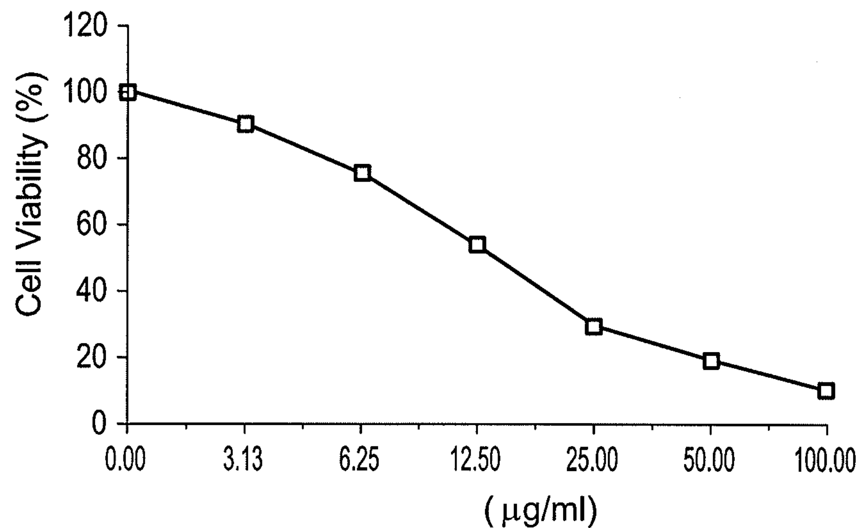
FIG. 6 is a graph of the cytotoxicity of katononic acid nanosheets to MCF-7 cells.

Table 1 demonstrates toxicity of katononic acid nanosheets to MCF-7 cells. These tests demonstrated an $IC_{50}$ of 23.5 μg/ml. These results are also illustrated in FIG. 6.

TABLE 1

% Viability of MCF-7 Cells Exposed to Katononic Acid Nanosheets

| Nanosheets | 1st | $2^{nd}$ | 3rd | Mean | % Inhibition | Std. Dev. (±) |
|---|---|---|---|---|---|---|
| 100 μg/ml | 11.68 | 10.49 | 9.73 | 10.63 | 89.37 | 0.98 |
| 50 μg/ml | 20.93 | 18.64 | 19.02 | 19.53 | 80.47 | 1.23 |
| 25 μg/ml | 31.74 | 29.62 | 27.41 | 29.59 | 70.41 | 2.17 |
| 12.5 μg/ml | 55.68 | 54.29 | 52.41 | 54.13 | 45.87 | 1.64 |
| 6.25 μg/ml | 76.53 | 70.84 | 79.58 | 75.65 | 24.35 | 4.44 |
| 3.125 μg/ml | 92.37 | 87.52 | 91.64 | 90.51 | 9.49 | 2.62 |

Figure 7:
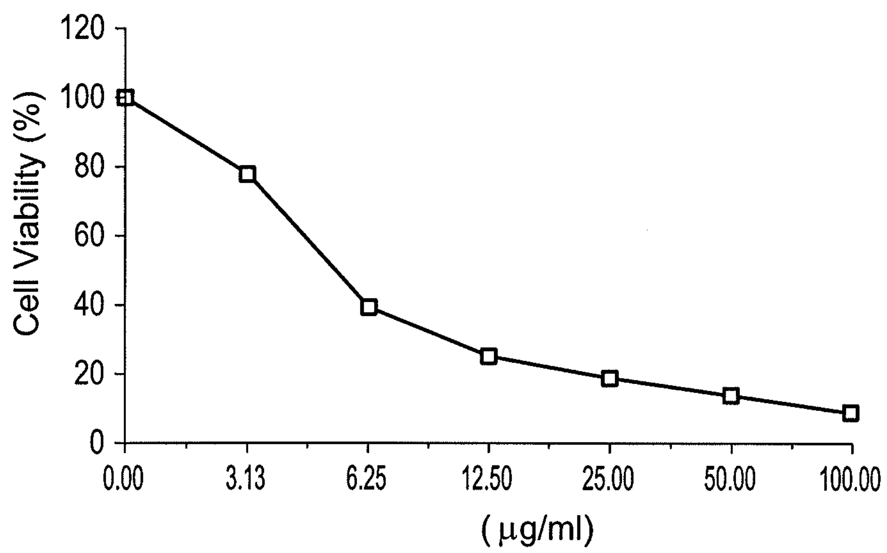
FIG. 7 is a graph of the cytotoxicity of katononic acid nanosheets to HepG-2 cells.

Table 2 demonstrates toxicity of katononic acid nanosheets to HepG-2 cells. These tests demonstrated an $IC_{50}$ of 5.4 μg/ml. These results are also illustrated in FIG. 7.

TABLE 2

% Viability of HepG-2 Cells Exposed to Katononic Acid Nanosheets

| Nanosheets | 1st | 2nd | 3rd | Mean | % Inhibition | Std. Dev. (±) |
|---|---|---|---|---|---|---|
| 100 μg/ml | 9.25 | 10.34 | 8.41 | 9.33 | 90.67 | 0.97 |
| 50 μg/ml | 15.39 | 14.87 | 12.32 | 14.19 | 85.81 | 1.64 |
| 25 μg/ml | 18.72 | 20.98 | 18.06 | 19.25 | 80.75 | 1.53 |
| 12.5 μg/ml | 23.64 | 28.23 | 24.15 | 25.34 | 74.66 | 2.52 |
| 6.25 μg/ml | 39.58 | 43.69 | 35.63 | 39.63 | 60.37 | 4.03 |
| 3.125 μg/ml | 81.36 | 76.45 | 75.89 | 77.90 | 22.10 | 3.01 |

Figure 8:
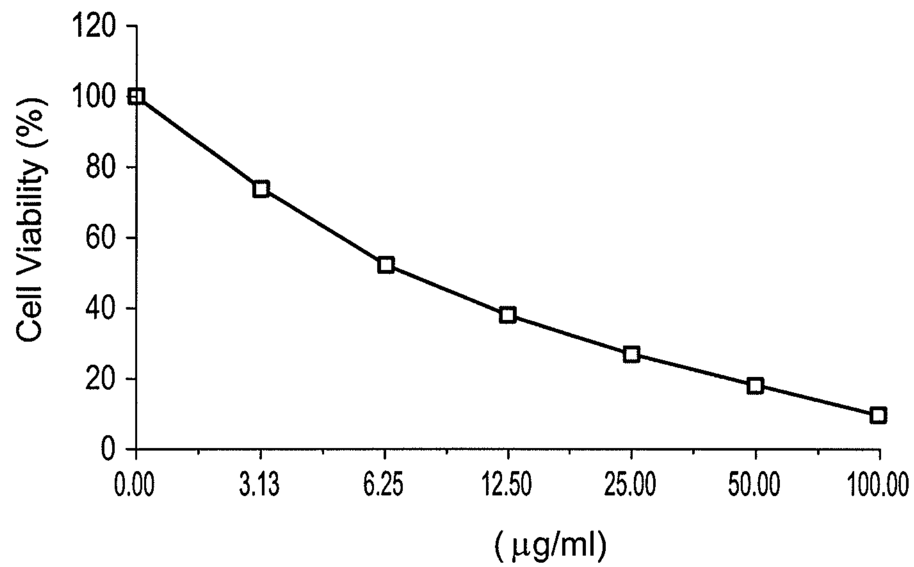
FIG. 8 is a graph of the cytotoxicity of katononic acid nanosheets to HCT-116 cells.

Table 3 demonstrates toxicity of Katononic acid nanosheets to HCT-116 cells. These tests demonstrated an $IC_{50}$ of 7.26 μl/ml. These results are also illustrated in FIG. 8.

TABLE 3

% Viability of HCT-116 Cells Exposed to Katononic Acid Nanosheets

| Nanosheets | 1st | 2nd | 3rd | Mean | % Inhibition | Std. Dev. (±) |
|---|---|---|---|---|---|---|
| 100 μg/ml | 11.78 | 8.61 | 9.24 | 9.88 | 90.12 | 1.68 |
| 50 μg/ml | 16.52 | 17.93 | 20.45 | 18.30 | 81.70 | 1.99 |
| 25 μg/ml | 25.23 | 28.84 | 27.12 | 27.06 | 72.94 | 1.81 |
| 12.5 μg/ml | 37.89 | 40.17 | 36.29 | 38.12 | 61.88 | 1.95 |
| 6.25 μg/ml | 51.72 | 56.28 | 48.85 | 52.28 | 47.72 | 3.75 |
| 3.125 μg/ml | 76.48 | 75.36 | 69.18 | 73.67 | 26.33 | 3.93 |

Figure 9:
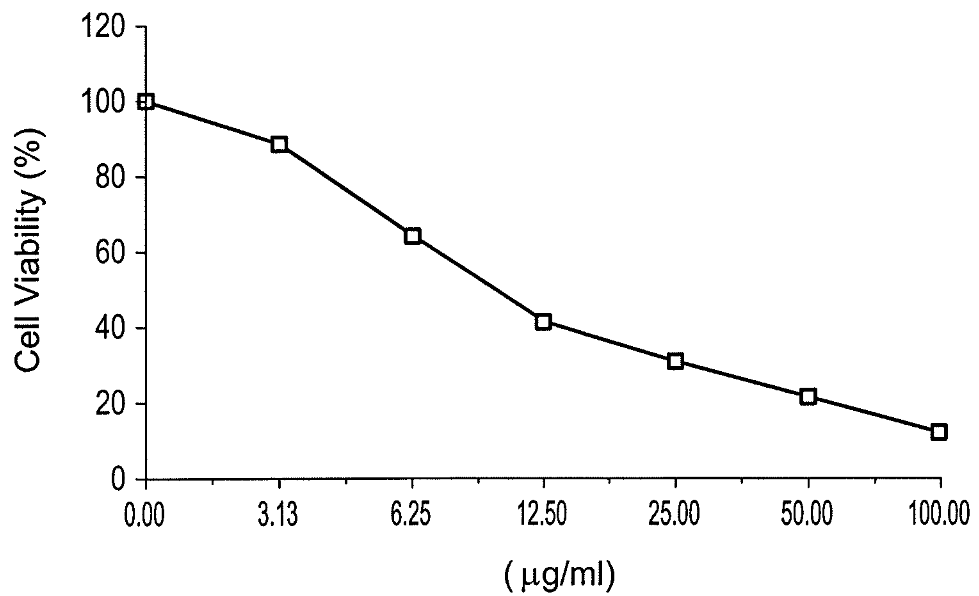
FIG. 9 is a graph of the cytotoxicity of katononic acid nanosheets to A549 cells.

Table 4 demonstrates toxicity of Katononic acid nanosheets to A549 cells. These tests demonstrated an $IC_{50}$ of 10.2 μg/ml. These results are also illustrated in FIG. 9.

TABLE 4

| % Viability of A549 Cells Exposed to Katononic Acid Nanosheets | | | | | | |
|---|---|---|---|---|---|---|
| Nanosheets | 1st | 2nd | 3rd | Mean | % Inhi-bition | Std. Dev. (±) |
| 100 μg/ml | 14.53 | 11.37 | 10.92 | 12.27 | 87.73 | 1.97 |
| 50 μg/ml | 23.94 | 19.41 | 21.85 | 21.73 | 78.27 | 2.27 |
| 25 μg/ml | 31.65 | 28.92 | 32.49 | 31.02 | 68.98 | 1.87 |
| 12.5 μg/ml | 46.32 | 37.16 | 40.83 | 41.44 | 58.56 | 4.61 |
| 6.25 μg/ml | 63.71 | 60.34 | 68.96 | 64.34 | 35.66 | 4.34 |
| 3.125 μg/ml | 89.48 | 87.65 | 89.13 | 88.75 | 11.25 | 0.97 |

Figure 10:
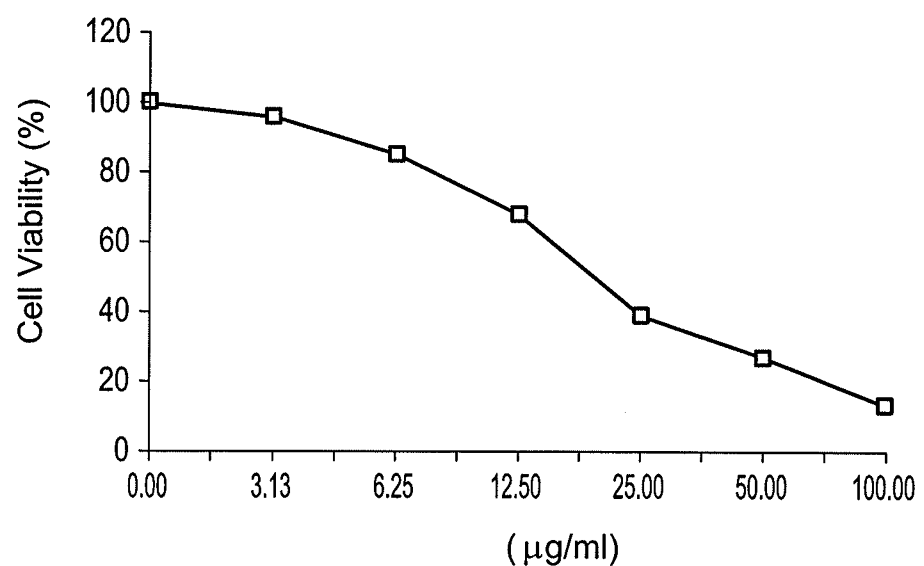
FIG. 10 is a graph of the cytotoxicity of katononic acid nanosheets to Hela cells.

Table 5 demonstrates toxicity of Katononic acid nanosheets to Hela cells. These tests demonstrated an $IC_{50}$ of 20.3 μg/ml. These results are also illustrated in FIG. 10.

TABLE 5

| % Viability of Hela Cells Exposed to Katononic Acid Nanosheets | | | | | | |
|---|---|---|---|---|---|---|
| Nanosheets | 1st | $2^{nd}$ | 3rd | Mean | % Inhi-bition | Std. Dev. (±) |
| 100 μg/ml | 13.98 | 11.72 | 15.83 | 13.84 | 86.16 | 2.06 |
| 50 μg/ml | 26.74 | 30.83 | 24.06 | 27.21 | 72.79 | 3.41 |
| 25 μg/ml | 38.62 | 39.14 | 39.84 | 39.20 | 60.80 | 0.61 |
| 12.5 μg/ml | 68.13 | 65.29 | 70.91 | 68.11 | 31.89 | 2.81 |
| 6.25 μg/ml | 89.25 | 81.47 | 85.23 | 85.32 | 14.68 | 3.89 |
| 3.125 μg/ml | 97.04 | 94.21 | 96.78 | 96.01 | 3.99 | 1.56 |

Example 4

Antimicrobial Activity

The antimicrobial effect of the katononic acid nanosheets was evaluated against gram positive bacteria, gram negative bacteria, and fungi. Testing results demonstrating the antimicrobial effects of katononic acid nanosheets are provided in Table 6. The diffusion agar technique was used with a well diameter of 6.0 mm and 100 μl of katononic acid nanosheets.

TABLE 6

| Antimicrobial Activity of Katononic Acid Nanosheets vs. Reference Drugs Zone of Inhibition (±SD) | | |
|---|---|---|
| Fungi | Nanosheets | Amphotericin B |
| *Absidia corymbffera* (RCMB 02564) | 14 ± 0.32 | 23.0 ± 0.10 |
| *Geotricum candidum* (RCMB 05097) | 16 ± 0.14 | 27.0 ± 0.20 |
| *Candida albicans* (RCMB 05036) | 13 ± 0.74 | 25.7 ± 0.10 |
| Gram Positive bacteria | Nanosheets | Ampicillin |
| *Staphylococcus aureus* (RCMB 010027) | 19 ± 0.43 | 27.3 ± 0.14 |
| *Staphylococcus epidermidis* (RCMB 010024) | 20.3 ± .22 | 25.0 ± 0.18 |
| *Streptococcus pyogenes* (RCMB 010015) | 15 ± 0.56 | 26.3 ± 0.34 |
| Gram Negative bacteria | Nanosheets | Gentamycin |
| *Proteous vulgaris* (RCMB 010085) | 13.3 ± .19 | 23.4 ± 0.30 |
| *Klebsiella pneumoniae* (RCMB 0010093) | 15 ± 0.11 | 26.4 ± 0.15 |
| *Salmonella enteritidis* (RCMB 010084) | 17 ± 0.38 | 25.2 ± 0.18 |

It is to be understood that the green synthesis of katononic acid nanosheets is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. A method of synthesizing katononic acid nanosheets, comprising:

extracting the aerial parts of *Nuxia oppositifolia* by maceration to produce an extract;

partitioning the extract to produce a fraction;

separating the fraction using column chromatography to produce at least one katononic acid subfraction;

crystallizing the at least one katononic acid subfraction to provide powdered katononic acid;

dissolving the powdered katononic acid in an alcohol to provide a dissolved katononic acid mixture; and adding the mixture to boiling water under ultrasonic conditions to produce a sonicated katononic acid solution;

stirring the sonicated katononic acid solution to provide a stirred katononic acid solution; and freeze drying the stirred katononic acid solution to produce katononic acid nanosheets.

2. The method of synthesizing of katononic acid nanosheets according to claim 1, further comprising harvesting the aerial parts of *N. oppositifolia* from Wadi Lajab, in the Jazan province of Saudi Arabia.

3. The method of synthesizing of katononic acid nanosheets according to claim 1, wherein the extract is partitioned with n-hexane and the fraction produced is an n-hexane fraction.

4. The method of synthesizing of katononic acid nanosheets according to claim 3, further comprising separating the n-hexane fraction by eluting the katononic acid containing subfraction with 10% EtOAc/n-hexane.

5. The method of synthesizing of katononic acid nanosheets according to claim 4, further comprising separating the n-hexane fraction by eluting an undesired subfraction using 5% EtOAc/n-hexane prior to eluting the katononic acid containing subfraction with 10% EtOAc/n-hexane.

6. The method of synthesizing of katononic acid nanosheets according to claim 1, wherein the powdered katononic acid is dissolved in methanol to provide the dissolved katononic acid mixture and about 5 ml of the dissolved katononic acid mixture is added to about 40 ml boiling water at a flow rate of about 0.1 to about 0.3 drops per minute for about 10 minutes under ultrasonic conditions.

7. The method of synthesizing of katononic acid nanosheets according to claim 1, wherein the mixture is sonicated for about 20 minutes, and the sonicated katononic acid solution is stirred for about 15 minutes.

8. A katononic acid nanosheet prepared according to the method of claim 1.

9. The katononic acid nanosheet of claim 8, wherein the katononic acid nanosheet has a diameter of about 137.2 nanometers.

10. A method of killing cancer cells, comprising contacting the cancer cells with the katononic acid nanosheet of claim 8.

11. The method of killing cancer cells of claim 10, wherein the cancer cells are human cancer cells.

12. The method of killing cancer cells of claim 10, wherein the cancer cells are selected from the group consisting of breast cancer cells, liver cancer cells, colon cancer cells, lung cancer cells, and cervical cancer cells.

13. A method of inhibiting microbial growth, comprising contacting a microbe with the katononic acid nanosheet of claim 8, the microbe including at least one of gram positive bacteria, gram negative bacteria, and fungi.

* * * * *